United States Patent [19]

Amjad

[11] Patent Number: 4,842,847
[45] Date of Patent: Jun. 27, 1989

[54] DENTAL CALCULUS INHIBITING COMPOSITIONS

[75] Inventor: Zahid Amjad, Avon Lake, Ohio

[73] Assignee: The B. F. Goodrich Company, Akron, Ohio

[21] Appl. No.: 135,803

[22] Filed: Dec. 21, 1987

[51] Int. Cl.⁴ ................................................ A61K 7/18
[52] U.S. Cl. ...................................... 424/52; 424/57
[58] Field of Search .................................. 424/52, 57

[56] References Cited

U.S. PATENT DOCUMENTS

| | | | |
|---|---|---|---|
| 3,966,863 | 6/1976 | Forward et al. | 424/52 |
| 4,122,163 | 10/1978 | Muhler et al. | 424/52 |
| 4,139,609 | 2/1979 | Schreilber | 424/52 |
| 4,152,420 | 5/1979 | Gaffar et al. | 424/52 |
| 4,272,513 | 6/1981 | Gaffar | 424/57 |
| 4,420,312 | 12/1983 | Wason | 51/308 |
| 4,430,323 | 2/1984 | Silver | 424/52 |
| 4,436,721 | 3/1984 | Gaffer | 424/52 |
| 4,565,691 | 1/1986 | Jackson | 424/57 |
| 4,627,977 | 12/1986 | Gaffar et al. | 424/52 |
| 4,732,617 | 3/1988 | Causton et al. | 424/52 |
| 4,772,461 | 9/1988 | Parran, Jr. et al. | 424/52 |

*Primary Examiner*—Paul Lieberman
*Assistant Examiner*—Willie J. Thompson
*Attorney, Agent, or Firm*—George A. Kap

[57] ABSTRACT

Oral compositions and a method for inhibiting dental calculus are disclosed herein, said compositions are characterized by the presence of a fluoride source, a dental abrasive, and an anti-calculus agent selected from polymeric homopolymers of a carboxylic monomer and copolymers thereof containing at least 30% of said carboxylic monomer.

17 Claims, No Drawings

DENTAL CALCULUS INHIBITING COMPOSITIONS

BACKGROUND OF THE INVENTION

This invention relates to oral compositions containing an anticalculus agent.

Tartar or dental calculus is calcified plaque and plaque is the culprit of gum disease. Dental calculus or tartar is a deposit which forms on the surfaces of the teeth at the gingival margin. Mature calculus consists of an inorganic portion which is largely calcium phosphate arranged in a hydroxyapatite crystal lattice structure similar to bone, enamel and dentine. An organic portion is also present and consists of salivary sediment, food debris, and various type of microorganisms.

It is generally agreed that calcium and orthophosphate form the crystalline material known as hydroxyapatite which is dental calculus, i.e., a mineralized, hard formation which forms on teeth. The precursor to crystalline hydroxyapatite is amorphous calcium phosphate which differs from hydroxyapatite in atomic structure, particle morphology, and stoichiometry. The x-ray diffraction pattern of amorphous calcium phosphate shows broad peaks typical of amorphous materials which lack the long range atomic order characteristics of all crystalline materials, including hydroxyapatite.

It is generally well known that linear molecularly dehydrated polyphosphates, such as hexametaphosphate, tripolyphosphate, pyrophosphate, and the like, are effective calcium and magnesium ion suppressors, inhibitors, sequestrants and/or chelating agents. Such materials are also known to be effective inhibitors of hydroxyapatite formation in vitro. It is also known that such polyphosphates, when introduced into the oral cavity and/or saliva, are significantly hydrolyzed by salivary enzymes, i.e., phosphatases, to orthophosphates which are ineffective as inhibitors of hydroxyapatite formation.

Studies have shown that there is a good correlation between the ability of a compound to prevent hydroxyapatite crystalline growth in vitro and its ability to prevent calcification in vivo, provided that such compound is stable in and inert to saliva and its components.

SUMMARY OF THE INVENTION

Oral compositions are characterized by the presence of a fluoride source, dental abrasive, and an anticalculus agent which is stable in the presence of saliva or salivary enzymes. The anticalculus agent is selected from homopolymers of a monounsaturated monocarboxylic and dicarboxylic acids of 3 to 5 carbon atoms and from copolymers containing at least 30% by weight of such acid, particularly acrylic acid. This invention is also directed to a method for inhibiting dental calculus by applying to the teeth one of the oral compositions disclosed herein. The anticalculus agents herein are effective in absence of germicidal composition.

DETAILED DESCRIPTION OF THE INVENTION

The oral compositions disclosed and claimed herein are characterized by the presence of a fluoride source, a dental abrasive or a polishing agent, a vehicle, and an anticalculus agent selected from homopolymers of monounsaturated monocarboxylic and dicarboxylic acids of 3 to 5 carbon atoms and from copolymers containing at least 30% by weight of a monounsaturated monocarboxylic or a dicarboxylic acid of 3 to 5 carbons, its anhydride, or a water-soluble salt of such acid. Comonomers which can be copolymerized with one or more of the acids include acrylamides, alkyl acrylates, alkyl itaconates, vinyl sulfonic acid, hydroxyalkyl acrylates, alkoxyalkyl acrylates, lower alkenyl carboxylates, styrene sulfonic acids, allyloxyhydroxyalkane sulfonic acids, acrylamidoalkane sulfonic acids, sulfoloweralkyl acrylates, polymerized vinyl alcohols, anhydrides and salts thereof. Such anticalculus agents can be used in conjunction with other additives, including other anticalculus agents. This invention is also directed to a method for inhibiting dental calculus by applying to the teeth a calculus-inhibiting amount of the oral composition described and claimed herein.

The homopolymers of the carboxylic acids, anhydrides and salts thereof, and the copolymers have molecular weight in the range of 400 to 100,000, preferably 500 to 50,000. The homopolymers have an especially preferred molecular weight of 500 to 50,000. The copolymers suitable herein are random non-crosslinked polymers. Molecular weight is measured by gel permeation chromatography. Amount of the anticalculus agent in the oral compositions claimed herein is about 0.01 to 10% by weight, preferably 0.1 to 5%.

As will be shown later, polyphosphates can function as polishing or abrasive agents. Although such polyphosphates are very effective against calculus in absence of enzyme found in saliva, in presence of enzyme, the polyphosphates are hydrolyzed to orthophosphates which are ineffective as anticalculus agents.

The sources of fluoride ions, or fluorine-providing compounds, required according to this invention as an essential component of the described composition, are well known in the art as anti-caries agents and also act as such agents in the practice of this invention. These compounds may be slightly soluble in water or may be fully water-soluble. They are characterized by their ability to release fluoride ions in water and by freedom from undesired reaction with other compounds of the oral preparation. Among these materials are inorganic fluoride salts, such as soluble alkali metal and alkaline earth metal salts, for example, sodium fluoride, potassium fluoride, ammonium fluoride, calcium fluoride, copper fluorides such as cuprous fluoride, zinc fluoride, barium fluoride, sodium fluorosilicate, ammonium fluorosilicate, sodium fluorozirconate, sodium monofluoro-phosphate, aluminum mono- and di-fluorophosphate, and fluorinated sodium calcium pyrophosphate. Alkali metal and tin fluorides, such as sodium and stannous fluoride, sodium monofluorophosphate, and mixtures thereof, are preferred.

The amount of fluorine-providing compound is dependent to some extent upon the type of compound, its solubility, and the type of oral composition, but it must be a nontoxic amount, generally about 0.005 to about 3.0% in the composition. In a dentifrice composition, e.g. gel, cream, toothpaste or toothpowder, an amount of such compound which released 50 to 3500 ppm of flourine ion by weight of the composition is considered satisfactory. Any suitable minimum amount of such compound may be used but it is preferable to employ sufficient compound to release about 300 to about 2,000 ppm, more preferably about 800 to about 1,500 ppm of fluoride ion. Typically, in the case of alkali metal fluorides and stannous fluoride, this component is present in an amount up to about 2% by weight, based on the weight of the composition, and preferably in the range of about 0.05% to 1%. In the case of sodium monofluorophosphate, the compound may be present in an amount of about 0.1–3%, more typically about 0.2–1%.

In oral compositions such as mouthwashes, lozenges and chewing gum, the fluorine-providing compound is typically present in an amount sufficient to release up to about 500 ppm, preferably about 25 to about 300 ppm by weight of fluoride ion. Generally, about 0.005 to about 1.0 weight percent of such compound is present.

Water employed in the preparation of commercially suitable oral compositions should preferably be of low ion content and free of organic impurities. Water comprises from about 2% to about 95%, preferably from about 20% to about 95% of the compositions of this invention. When in the form of toothpastes, the amount of water is preferably from about 2% to about 45%, while mouthwashes preferably contain from about 45% to about 95%.

In a toothpaste, the liquid vehicle may comprise water and humectant typically in an amount ranging from about 10% to about 90% by weight of the preparation. Glycerine, propylene glycol, sorbitol, polypropylene glycol and/or polyethylene glycol exemplify suitable humectants or carriers. Also advantageous are liquid mixtures of water, glycerine and sorbitol. In clear gels, where the refractive index is an important consideration, about 3–30% by weight of water, 0 to about 80% weight of glycerine, and about 20–80% by weight of sorbitol, is preferably employed.

In certain desirable forms of this invention, the oral compositions may be substantially solid or pasty in character, such as toothpowder, a dental tablet, toothpaste, gel or dental cream. The vehicle of such solid or pasty oral preparations generally contains a polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, aluminum silicate, zirconium silicate, silica, bentonite, and mixtures thereof. Other suitable polishing materials include the particulate thermosetting resins described in U.S. Pat. No. 3,070,510 such as formaldehydes of melamine, phenol, and urea, and cross-linked polyepoxides and polyesters. Preferred polishing materials include crystalline silica having particle sizes of up to about 5 microns, a mean particle size of up to about 1.1 microns, and a surface area of up to about 50,000 cm$^2$/gm, silica gel or colloidal silica, and complex amorphous alkali metal aluminosilicate.

When visually clear gels are employed, a polishing agent of colloidal silica and alkali metal alumino-silicate complexes are particularly useful since they have refractive indices close to the refractive indices of the liquid gelling agent.

The linear, molecularly dehydrated polyphosphate salts operative herein as abrasive dental additives are well known, being generally employed in the form of their wholly or partially neutralized water soluble alkali metal or ammonium salts and mixtures thereof. Representative examples include sodium hexametaphosphate, sodium tripolyphosphate, disodium diacid, trisodium monoacid, and tetrasodium pyrophosphates, and the like. Linear polyphosphates correspond to $(NaPO_3)_n$ where n is about 2 to about 125. They are generally employed in the instant oral compositions in approximate weight amounts of 0.1 to 7%, preferably 1 to 5%.

The polishing material or dental abrasive is generally present in the solid or pasty compositions in weight concentrations of about 10% to about 99%. Preferably, it is present in amounts ranging from about 10% to about 75% in toothpaste, and from about 70% to about 99% in toothpowder.

Toothpastes, creams and gels typically contain a natural or synthetic thickener or gelling agent in proportions of about 0.1 to about 10, preferably about 0.5 to about 5, weight percent. A suitable thickener is synthetic hectorite, a synthetic colloidal magnesium, alkali metal silicate complex clay, and carboxyvinyl polymer or polyacrylic acid of intermediate molecular weight.

The oral compositions of this invention can contain a variety of optional conventional oral ingredients. Such optional ingredients include sudsing agents, flavoring agents, sweetening agents, binding agents, coloring agents, humectants, and pigments.

A preferred optional ingredient is a sudsing agent. Suitable sudsing agents are those which are reasonably stable and form suds throughout a wide pH range, i.e., non-soap anionic, cationic, zwitterionic and amphoteric organic synthetic detergents. Sudsing agents of these types are described more fully in Agricola et al U.S. Pat. No. 3,959,458 and in Haefele U.S. Pat. No. 3,937,807.

Flavoring agents can also be added to the instant compositions. Suitable flavoring agents include oil of wintergreen, oil of peppermint, oil of spearmint, oil of sassafras, and oil of clove. Sweetening agents which can be used include saccharin, dextrose, levelose, aspartame, D-tryptophan, dihydrochalcones, acesulfame and sodium cyclamate. Flavoring agents are generally used in the compositions at level of from about 0.4% to about 2% by weight and sweetening agents at level of from about 0.1% to about 5% by weight.

Binders can also be used with the toothpastes of the present inventions. Such binders include, for example, xanthan gum, carrageenan (Irish moss), and carboxyvinyl polymers or polyacrylic acids of intermediate molecular weight. These binders are generally present at a level of from about 0.1% to 1%.

Another optional component of the compositions herein is a humectant. The humectant serves to keep the toothpaste compositions from hardening upon exposure to air and in mouthwashes, give a moist feel to the mouth. Certain humectants can also impart desirable sweetness or flavor to mouthwash and toothpaste compositions. The humectant, on a pure humectant basis, generally comprises from about 0% to 70%, preferably from about 5% to 55%, by weight of the compositions herein.

Suitable humectants for use in this invention include edible polyhydric alcohols such as glycerine, sorbitol, xylitol and propylene glycol. Sorbitol is frequently employed as a 70% aqueous solution.

The mouthwashes herein may also contain ethanol in an amount of from about 0 to about 30%, preferably 5 to 25%, as a germicide.

The pH of the compositions herein is in the range of 6 to 10, preferably from 7 to 9. The pH is preferably achieved through a proper balancing of the pyrophosphate salts or by the addition of an alkaline or acidic agent.

The compositions herein are made using conventional mixing techniques.

The anticalculus agents of interest herein are selected from homopolymers of monounsaturated monocarboxylic and dicarboxylic acids of 3 to 5 carbon atoms and from copolymers of such an acid, anhydrides and salts thereof, with at least one principal conomer selected from acrylamides, alkyl acrylates, alkyl itaconates, vinyl sulfonic acid, hydroxyalkyl acrylates, alkoxyalkyl acrylates, lower alkenyl carboxylates, styrene sulfonic acids, allyloxyhydroxyalkane sulfonic acids, acrylamidoalkane sulfonic acids, sulfoloweralkyl acrylates, polymerized vinyl alcohols, anhydrides and salts thereof.

As used herein, generic term "acrylates" also includes "methacrylates".

A fluoride source, a dental abrasive and vehicle selected from water or water plus a humectant, as well as an anticalculus agent, are essential ingredients of the oral compositions of this invention.

In certain forms of the invention, the oral composition may be substantially liquid in character, such as mouthwash or rinse. In such a composition, the vehicle is typically a water-alcohol mixture which desirably includes a humectant. Generally, the weight ratio of water to alcohol is is the range of from about 1:1 to about 20:1, preferably about 3:1 to 10:1 and more preferably about 4:1 to about 6:1. The total amount of water-alcohol mixture in this type of preparation is typically in the range of from about 70% to about 99.9% by weight of the preparation.

The carboxylic copolymers referred to above are copolymers of a carboxylic acid, salts and anhydrides thereof and at least one principal copolymerizable monomer. The copolymers can also include up to about 30%, preferably 2 to 10%, of at least one secondary copolymerizable monomer as long as such secondary comonomer does not substantially deleteriously affect performance of the copolymers defined above as anticalculus agents.

The anticalculus carboxylic copolymers contain at least 30% by weight of the carboxylic monomer, in acid or anhydride or salt form, preferably 40 to 99%. The principal comonomer is used at the level of up to about 80%, preferably 1 to 60%. The principal comonomer and the carboxylic monomer form the copolymer unless the secondary monomer is used. The secondary comonomer, if used, is used in place of a portion of the principal comonomer.

The principal comonomers are selected from acrylamides, alkyl acrylates, alkyl itaconates, vinyl sulfonic acids, hydroxyalkyl acrylates, alkoxyalkyl acrylates, lower alkyl carboxylates, styrene sulfonic acids, allyloxyhydroxyalkane sulfonic acids, sulfoloweralkyl acrylates, polymerized vinyl alcohols, and anhydrides and salts thereof.

Suitable carboxylic monomers are selected from monounsaturated carboxylic acids of 3 to 5 carbons, anhydrides and salts thereof, which have at least one activated olefinic double bond and at least on carboxyl group. Monocarboxylic and dicarboxylic acids are preferred.

Illustrative of such acids are acrylic, methacrylic, ethacrylic, alpha-chloroacrylic, crotonic, beta-acryloxy propionic, sorbic, alpha-chlorosorbic, cinnamic, beta-styrylacrylic, muconic, itaconic, citraconic, mesaconic, glutaconic, aconitic, alpha-phenylacrylic, 2-benzyl acrylic, 2-cyclohexyacrylic, angelic, umbellic, fumaric, maleic acids and anhydrides. The preferred carboxylic acids are selected from acrylic acid, methacrylic acid, itaconic acid, maleic acid and its anhydride, citraconic acid, and mesaconic acid, especially acrylic acid, methacrylic acid, itaconic acid maleic acid and maleic anhydride. The acrylic and methacrylic acid are especially preferred.

Suitable acrylamides as principal comonomers are defined as follows:

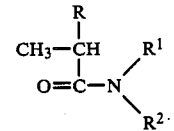

where R is hydrogen or methyl and $R^1$ and $R^2$ are individually selected from hydrogen, alkyl and substituted alkyl groups each containing a total of 1 to 12, preferably 1 to 8 carbons. Preferred acrylamides are the substituted acrylamides where either $R^1$ or $R^2$ is not hydrogen. Substituents on the alkyl groups include alkyl, aryl, hydroxyl, hydroxylakyl, carboxylic acid, and keto groups. Specific examples of substituted acrylamides include t-butyl acrylamide, isopropyl acrylamide, isobutyl acrylamide, methyl acrylamide, t-butyl methacrylamide, 2-(2,4,4-trimethyl penty) acrylamide, 2-(2-methyl-4-oxopentyl) acrylamide, hydroxymethyl acrylamide, hydroxypropyl acrylamide, diacetone acrylamide, and 3-acrylamido-3-methyl butanoic acid.

The alkyl acrylates as principal comonomers are defined as follows:

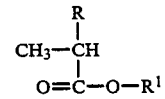

where R is hydrogen or methyl and $R^1$ is selected from alkyl groups of 1 to 6 carbons and substituted alkyl groups where $R^1$ is defined as $R^2—Y$, where $R^2$ is an alkyl group containing from 1 to 6 carbon atoms and Y is $—SO_3X$, $—C(O)R^3$, or $—CO_2X$ where X is hydrogen, alkali metal, alkaline earth metal, or ammonium, and $R^3$ is alkyl of 1 to 3 carbon atoms. In a preferred embodiment, the $R^1$ group is unsubstituted of 1 to 4 carbon atoms. Specific examples os suitable monomeric alkyl acrylates and methacrylates include ethyl acrylate, ethyl methacrylate, sulfoproyl acrylate, and carboxyethyl acrylate.

The alkyl ataconates as principal comonomers in have the following structure:

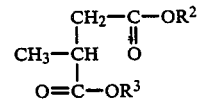

where $R^2$ and $R^3$ are individually selected from hydrogen, alkyl and substituted alkyl groups of 1 to 12 carbon atoms in the alkyl group, provided that both $R^2$ and $R^3$ are not hydrogen although either $R^2$ or $R^3$ can be hydrogen. Substituents on the $R^2$ and $R^3$ groups include lower alkyl, aryl such as phenyl, and keto groups, however, in a preferred embodiment, $R^2$ and $R^3$ are individually selected from unsubstituted lower alkyl groups of 1 to 4 carbon atoms. Specific examples of preferred $R^2$ and $R^3$ groups include methyl, ethyl, propyl, isopropyl, butyl and isomeric forms thereof, and the like. Preferred herein are the diesters of itaconic acid. Specific examples of preferred itaconic acid esters include dimethyl itaconate, diethyl itaconate and dibutyl itaconate.

Vinyl sulfonic acid and salts thereof of the principal comonomers are defined as follows:

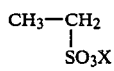

where X is selected from hydrogen, alkali metal, alkaline earth metal, and ammonium groups, preferably an alkali metal and ammonium groups. Preferred vinyl sulfonic acid salt is sodium vinyl sulfonate where X in the above formula is sodium.

Hydroxyalkyl acrylates of the principal comonomers are defined as follows:

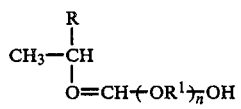

where R is hydrogen or a lower alkyl of 1 to 3 carbon atoms, preferably hydrogen or methyl; $R^1$ is selected from lower alkylene groups of 2 to 4, preferably 2 to 3 carbon atoms; and n is an integer from 1 to 5. Some specific examples of suitable hydroxylakyl acrylates include hydroxypropyl acrylates and hydroxypropyl methacrylate.

The alkoxyalkyl acrylates of the principal comonomers are defined as follows:

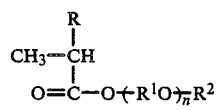

where R is hydrogen or methyl, $R^1$ is an alkylene group containing from 2 to 4, but preferably 2 to 3 carbon atoms, n is an integer from 1 to 5 but preferably 1 to 3, and $R^2$ is an alkyl group containing from 1 to 10 preferably 1 to 4 carbon atoms. Specific examples of alkoxyalkyl acrylate monomers include methoxyethyl acrylate, cellosolve methacrylate, and 2-(2-ethoxyethoxy) ethyl acrylate.

The vinyl carboxylate monomers are defined as follows:

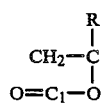

where R is hydrogen or a lower alkyl group of 1 to 6 carbon atoms, preferably hydrogen or alkyl of 1 to 2, and $R^1$ is selected from alkyl groups of 1 to 12 carbon atoms, preferably 1 to 8. The vinyl carboxylates, in polymerized form, can be hydrolyzed to contain polymerized vinyl alcohol repeating units of the following structure:

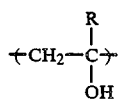

where R is hydrogen or a lower alkyl group of 1 to 6 carbon atoms, preferably hydrogen or alkyl of 1 to 2. The R group of the hydrolyzed carboxylates corresponds to the R group on the vinyl carboxylates. Specific examples of vinyl carboxylates include vinyl acetate, vinyl propionate, and 2-propenyl acetate.

Styrene sulfonic acids and salts thereof of the principal comonomers are defined as follows:

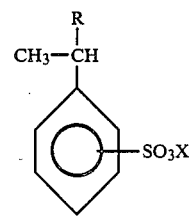

where R is hydrogen or a lower alkyl group of 1 to 6 carbon atoms, but preferably hydrogen, and X is hydrogen, alkali metal or alkaline earth metal or ammonium but particularly hydrogen, ammonium or alkali metal. A particularly suitable sulfonic acid is styrene sulfonic acid where R is hydrogen and the —$SO_3$ group is at the 3 or 4 position on the phenyl ring. The salts of styrene sulfonic acids are water-soluble. The sodium salt of styrene sulfonic acid is available commercially.

The allyloxyhydroxyalkane sulfonic acids and salts thereof of the principal comonomers are defined as follows:

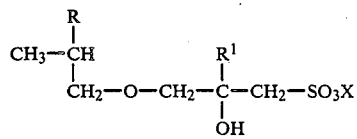

where R and $R^1$ are each hydrogen or methyl, and X is selected from hydrogen, alkali metal, alkaline earth metal and ammonium groups. Preferred monomers in this group is 3-allyloxy-2-hydroxypropanesulfonic acid, sodium salt.

Suitable acrylamidoalkane sulfonic acids and salts thereof of the principal comonomers have the general formula

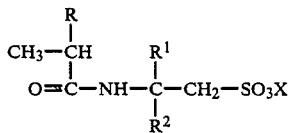

where R is hydrogen or methyl; X is selected from hydrogen, ammonium, alkali metals or alkaline earth metals, particularly hydrogen, ammonium, or an alkali metal; and $R^1$ and $R^2$ are individually selected from hydrogen and alkyl groups of 1 to 4 carbon atoms. In a preferred embodiment, R is hydrogen and $R^1$ and $R^2$ are each an alkyl group of 1 to 3 carbon atoms. The letter X in the above structural formula represents hydrogen or any metal cation which does not adversely affect the water solubility of the polymer, such as sodium, potassium and ammonium cations. In addition, X may also represent calcium, magnesium, and lithium, since they do not present any adverse effects on the solubility of the polymer. The acrylamidoalkane sulfonic acid monomer which has been found to be particularly suitable in accordance with the present invention is 2-acrylamido-2-methylpropane sulfonic acid which has the following structural formula:

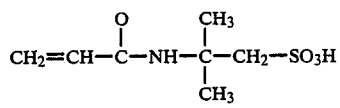

Sulfoalkyl acrylates of the principal comonomers have the following structure:

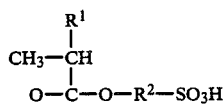

where $R^1$ is selected from hydrogen, methyl and the group

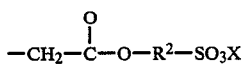

where $R^2$ is selected from alkylene groups of 1 to 12 carbons, preferably 2 to 4 carbons; and where X is selected from hydrogen, alkali metals, alkaline earth metals, and ammonium but particularly hydrogen, sodium, potassium, calcium, magnesium, and ammonium. The sulfo group $-SO_3X$, is preferably located on the last carbon atom of the $R^2$ group. The $R^2$ group can be substituted or unsubstituted. Substituents on the $R^2$ group are selected from those substituents which do not adversely affect the anticalculus activity of the copolymer. Preferred sulfoalkyl acrylates include 2-sulfoethyl methacrylate, 3-sulfopropyl acrylate, 3-sulfopropyl methacrylate, bis-(3-sulfopropyl) itaconate.

The monomers can be prepared, if desired, in a conventional manner but they are commercially available and, therefore, can be purchased. Polymerization of the monomers results in an essentially non-crosslinked random copolymer, the molecular weight of which can be adjusted with a little trial and error. The copolymer is preferably formed in a high yield ranging from about 50% to about 99% by weight of the comonomers.

It is also a requirement that the copolymer agent be soluble in water. Thus, high solubility of the agents is not essential but desirable. The anticalculus agent can be shipped in drums as a concentrated aqueous solution containing in the range of about 20% to about 50% by weight of solids per 100 parts of solution, which requires solubility to the extent of at least 20 weight parts per 100 parts of water.

Polymerization of the monomers identified herein can be carried out in a mutual solvent for both, such as in a lower alkanol of about 1 to 6 carbon atoms, or in water, with an effective amount of a free radical initiator sufficient to produce the desired composition within an acceptable period of time. The monomeric acids can be used as such or can be in a partially or a completely neutralized form prior to polymerization.

The reaction is conveniently carried out in water as the only reaction medium at a temperature in the range of about 30° to about 130° C. usually at atmospheric or slightly elevated pressure. The concentration of the copolymer formed may range from about 5% to about 50% by weight, based on total solids, which solution can be shipped directly.

The copolymers suitable herein as anticalculus agents have weight average molecular weight in the range of about 400 to about 100,000, and preferably about 5,000 to about 50,000, as determined by gel permeation chromatography. The acid numbers of the copolymers formed, as determined by a conventional titration with KOH, may range from about 230 to about 740, corresponding to a weight fraction of from 30% to about 95% by weight of monomer units having COOH groups. The preferred polymers have more than 50% by weight of free carboxyl groups and an acid number in the range of about 390 to about 700.

The following examples further describe and demonstrate preferred embodiments within the scope of the present invention. The examples are given solely for the purpose of illustration and are not to be construed as limitations of this invention. Many variations thereof are possible without departing from the invention's spirit and scope.

EXAMPLE I

Calcium phosphate precipitation was studied pursuant to the pH-stat technique described in Ex. 1 of U.S. Pat. No. 4,627,977. The rate of formation of hydroxyapatite (HAP) was followed titrimetrically by the consumption of sodium hydroxide using the pH-stat instrument of Brinkman Instruments Type 600 series.

Solutions of calcium chloride, sodium phosphate, and other components were mixed and stirred at a constant temperature of 37° C., and the amount of sodium hydroxide required to keep the pH constant at 7.40 was then continuously recorded as a function of time. Nitrogen gas presaturated with $H_2O$ at 37° C. was bubbled through the solution to exclude carbon dioxide. In this system, it is believed that the precipitation and crystal growth occur in two distinct stages. The first stage, which corresponds to the initial rise in consumption of sodium hydroxides represents the formation of amorphous calcium phosphate, which is less basic than hydroxayatite, whereas the second stage, which corresponds to the second rise in consumption of sodium hydroxide, represents the crystal growth of hydroxayantite.

Table A, below, sets forth results of the tests wherein pH was 7.40, temperature 37° C., and calcium ion and phosphate ion concentrations were each $3.2 \times 10^{-3}$M, and the composition of the anticalculus agents is given on weight basis:

TABLE A

| Anticalculus Agent | Composition | Mol. Wt. | Dosage (ppm) | Time of Crystal Growth Inhibition (minutes) |
|---|---|---|---|---|
| None | — | — | 0 | 3 |
| AA | 100 | 9,000 | 25 | 3 |
| AA | 100 | 9,000 | 55 | 4 |
| AA | 100 | 9,000 | 70 | 17 |
| AA:MAA:t-BuAm | 60:20:20 | 10,000 | 10 | 3 |
| AA:MAA:t-BuAm | 60:20:20 | 10,000 | 25 | 4 |
| AA:MAA:t-BuAm | 60:20:20 | 10,000 | 55 | 58 |
| AA:MAA:t-BuAm | 60:20:20 | 10,000 | 60 | 135 |
| AA:MAA:t-BuAm | 60:20:20 | 10,000 | 70 | 600+ |
| AA:MAA:t-BuAm | 60:20:20 | 10,000 | 100 | 1200+ |
| ME:MAn | 50:50 | — | 25 | 3 |
| ME:MAn | 50:50 | — | 55 | 3 |
| ME:MAn | 50:50 | — | 70 | 4 |
| ME:MAn | 50:50 | — | 150 | 4 |

TABLE A-continued

| Anticalculus Agent | Composition | Mol. Wt. | Dosage (ppm) | Time of Crystal Growth Inhibition (minutes) |
|---|---|---|---|---|
| AA:t-BuAm | 80:20 | 3,000 | 55 | 68 |
| AA:t-BuAm | 80:20 | 6,000 | 55 | 25 |
| AA:MAA:t-BuAm | 60:20:20 | 10,000 | 55 | 58 |
| AA:MAA:t-BuAm | 60:20:20 | 40,000 | 55 | 87 |
| AA:MAA:Am:CA | 54:21:9:16 | 6,000 | 55 | 60 |
| AA:MAA:Am:CA | 54:21:9:16 | 10,000 | 55 | 47 |
| AA:MAA:Am:CA | 54:21:9:16 | 19,000 | 55 | 38 |
| AA | 100 | 6,000 | 55 | 22 |
| AA | 100 | 2,100 | 55 | 100 |
| AA | 100 | 9,000 | 55 | 4 |
| AA | 100 | 5,100 | 55 | 45 |
| AA | 100 | 11,000 | 55 | 5 |
| AA | 100 | 60,000 | 55 | 3 |
| AA:t-BuAm | 90:10 | 6,000 | 55 | 55 |
| AA:t-BuAm | 80:20 | 6,000 | 55 | 25 |
| AA:t-BuAm | 60:40 | 6,000 | 55 | 25 |
| AA:AMPS | 80:20 | 10,000 | 55 | 17 |
| AA:AMPS | 51:49 | 10,000 | 55 | 45 |
| AA:AMPS | 10:90 | 10,000 | 55 | 8 |
| AA | 100 | 6,000 | 55 | 22 |
| AA | 100 | 9,000 | 55 | 4 |
| AA:EA | 80:20 | 6,000 | 55 | 64 |
| AA:EoTgA | 80:20 | 6,000 | 55 | 60 |
| AA:MMA | 80:20 | 10,000 | 55 | 37 |
| AA:DMI | 80:20 | 10,000 | 55 | 45 |
| AA:DEI | 70:30 | 10,000 | 55 | 25 |
| AA:SSS | 70:30 | 5,000 | 55 | 18 |
| AA:HPA | 63:37 | 7,000 | 55 | 48 |
| AA:Am | 45:55 | 6,000 | 55 | 10 |
| AA:DmAm | 60:40 | 6,000 | 55 | 60 |
| AA:t-BuAm | 60:40 | 6,000 | 55 | 25 |
| AA:AMPS | 51:49 | 10,000 | 55 | 45 |
| AA:COPS | 70:30 | 10,000 | 55 | 15 |
| AA:SEM | 80:20 | 10,000 | 55 | 55 |
| AA:SPM | 80:20 | 10,000 | 55 | 47 |
| AA:MAA:EMA | 60:20:20 | 10,000 | 55 | 38 |
| AA:AMPS:EMA | 60:20:20 | 10,000 | 55 | 43 |
| AA:AMPS:HPA | 60:10:30 | 7,000 | 55 | 40 |
| AA:AMPS:t-BuAm | 60:20:20 | 10,000 | 55 | 55 |
| AA:MAA:CHPM | 60:20:20 | 6,000 | 55 | 40 |
| AA:MAA:t-oAm | 60:30:10 | 10,000 | 55 | 40 |
| AA:SSS:SEM | 60:20:20 | 10,000 | 55 | 13 |
| AA:AMPS:Am | 60:20:20 | 10,000 | 55 | 54 |
| AA:AMPS:SSS | 60:30:10 | 10,000 | 55 | 23 |
| AA:AMPS:SSS | 60:30:10 | 12,000 | 55 | 28 |
| AA:MAA:Am:CA | 54:21:9:16 | 10,000 | 55 | 47 |
| MA | 100 | 500 | 55 | 240 |
| AA:MA | | | | 30 |
| AA:VAc | 80:20 | 10,000 | 55 | 25 |
| AA:VOH | 80:20 | 10,000 | 55 | 14 |
| AA:VAc:AMPS | 50:20:30 | 10,000 | 55 | 17 |
| AA:VOH:AMPS | 50:20:30 | 10,000 | 55 | 12 |

In Table A, the following contractions appear:
AA=acrylic acid
ME:MAn=methoxyethylene:maleic anhydride
t-BuAm=tertiary butyl acrylamide
MAA=methacrylic acid
HPA=hydroxypropyl acrylate
AMPS=2-acrylamido-2-methylpropane sulfonic acid
CA=2-(2-ethoxyethoxy)ethyl acrylate
Am=acrylamide
EA=ethyl acrylate
EoTgA=ethoxytriglycol acrylate
MMA=methyl metheacrylate
DMI=dimethyl itaconate
DEI=diethyl itaconate
IA=itaconic acid
SSS=sodium styrene sulfonate
DMA=dimethyl acrylate
COPS=3-allyloxy-3-hydroxypropane sulfonate
SEM=2-sulfoethyl methacrylate
SPM=3-sulfopropyl methacrylate
EMA=ethyl methacrylate
CHPM=chlorohydroxypropyl methacrylate
t-OAm=tertiary octyl acrylamide
MA=maleic anhydride
AA:MA=acrylic acid: maleic anhydride (Belclene 283, product of Ciba-Geigy)
VAc=vinyl acetate
VOH=vinyl alcohol
SPA=3-sulfopropyl acrylate
SPI=bis-3-sulfopropyl itaconate
MeOEA=methoxyethyl acrylate The copolymer of methoxyethylene and maleic anhydride used in above experiments was Gantrez S-97 resin. The column identified as "Time of Crystal Growth Inhibition" indicates crystal growth of hydroxyapatite.

The results in Table A generally indicate effectiveness as anticalculus agents, in absence of an enzyme, of homopolymers and copolymers of monounsaturated monocarboxylic and dicarboxylic acaids of 3 to 5 carbon atoms, particularly acrylic acid, maleic acid, and itaconic acid. Time of crystal growth inhibition exceeding 10 minutes is acceptable but in preferred embodiments, the time is in excess of about one half hour. Of course, this time period can be increased by increasing amount of the agent.

EXAMPLE II

Enzymatic hydrolysis was conducted in a 25 ml buffered solution of tris(hydroxymethyl)aminomethane-HCl, $2.5 \times 10^{-3}$M at pH=7.20 containing 12.5 ppm of pyrophosphate. A known amount (0–100 ppm) of anticalculus agent of this invention was added to pyrophosphate solution followed by the addition of inorganic pyrophosphatase enzyme. Solutions were continuously stirred at 25° C. After 3 hours, solutions were analyzed for orthophosphate using standard colorimeteric method. Inhibition of enzymatic hydrolysis by anticalculus agent was calculated according to the following equation:

$$\text{enzymatic hydrolysis inhibition} = \frac{(\text{phosphate})_c - (\text{Phosphate})_a}{(\text{Phosphate})_c}$$

where $(\text{phosphate})_c$ and $(\text{phosphate})_a$ represent orthophosphate concentrations in the absence and presence of anticalculus agent, respectively.

Results from triplicate experiments in the absence of anticalculus agent showed the amount of orthophosphate released during enzymatic hydrolysis was greater than 95% of the available orthophosphate. Results showing effectiveness of the anticalculus agents in the presence of enzyme, are set forth in Table B, below:

TABLE B

| Anticalculus Agent | Composition | Mol. Wt. | Dosage (ppm) | Enzymatic Hydrolysis Inhibition (%) |
|---|---|---|---|---|
| None | — | — | 0 | 0 |
| Me:MAn | 50:50 | — | 5 | 0 |
| MeOE:MA | 50:50 | — | 15 | 9 |
| MeOE:MA | 50:50 | — | 20 | 60 |
| MeOE:MA | 50:50 | — | 25 | 70 |
| MEOE:MA | 50:50 | — | 100 | 92 |
| AA:MAA:t-BuAm | 60:20:20 | 10,000 | 10 | 70 |
| AA:MAA:t-BuAm | 60:20:20 | 10,000 | 25 | 76 |
| AA:MAA:t-BuAm | 60:20:20 | 40,000 | 10 | 67 |
| AA:MAA:t-BuAm | 60:20:20 | 40,000 | 15 | 81 |

TABLE B-continued

| Anticalculus Agent | Composition | Mol. Wt. | Dosage (ppm) | Enzymatic Hydrolysis Inhibition (%) |
|---|---|---|---|---|
| AA:MAA:t-BuAm | 60:20:20 | 40,000 | 25 | 98 |
| AA:HPA | 63:37 | 7,000 | 10 | 47 |
| AA:HPA | 63:37 | 7,000 | 15 | 82 |
| AA:AMPS | 51:49 | 10,000 | 15 | 31 |
| AA:SPA | 80:20 | 10,000 | 15 | 83 |
| AA:DEI | 70:30 | 10,000 | 15 | 86 |
| AA:IA | 50:50 | 10,000 | 15 | 88 |
| AA:SPM | 80:20 | 10,000 | 15 | 90 |
| AA:AMPS:HPA | 60:10:30 | 10,000 | 15 | 76 |
| AA:AMPS:EMA | 60:20:20 | 10,000 | 15 | 59 |
| AA:AMPS:t-BuAm | 60:20:20 | 10,000 | 15 | 70 |
| AA:MA | — | — | 15 | 56 |
| AA:SEM | 80:20 | 10,000 | 15 | 81 |
| AA:SPI | 80:20 | 10,000 | 15 | 87 |
| AA:EoTgA | 80:20 | 6,000 | 15 | 80 |
| AA:EA | 80:20 | 6,000 | 15 | 79 |
| AA:AMPS:SSS | 60:20:20 | 10,000 | 15 | 76 |
| AA:VAc | 80:20 | 10,000 | 15 | 85 |
| AA:VOH | 80:20 | 10,000 | 15 | 86 |
| AA:AMPS:VoAc | 50:30:20 | 10,000 | 15 | 81 |
| AA:AMPS:VoOH | 50:30:20 | 10,000 | 15 | 87 |
| MA | 100 | 500 | 25 | 68 |
| MA | 100 | 500 | 15 | 51 |
| MA:SSS | — | — | 15 | 49 |
| AA:t-BuAm | 80:20 | 3,000 | 15 | 67 |
| AA:t-BuAm | 80:20 | 6,000 | 15 | 81 |
| AA:DMAm | 60:40 | 6,000 | 15 | 79 |
| AA:MeOEA | 80:20 | 6,000 | 15 | 90 |
| AA:AMPS:MeOEA | 60:20:20 | 10,000 | 15 | 86 |
| AA:SSS | 70:30 | 5,000 | 15 | 94 |
| AA:COPS | 70:30 | 10,000 | 15 | 90 |
| AA | 100 | 2,000 | 15 | 79 |
| AA | 100 | 60,000 | 15 | 89 |
| IA | 100 | 10,000 | 15 | 92 |

The data shown in Table B, above, illustrates the effectiveness of the homopolymers and copolymers to suppress the enzymatic hydrolysis of pyrophosphate. Th data also demonstrates the superior performance of the agents of this invention relative to the prior art methoxyethylene:maleic anhydride resin (Gantrez S-97).

In Table B, the same contractions apply as in Table A except IA represents itaconic acid and MA:SSS represents product of National Starch Corporation known as Versa TL-7 which is believed to be a copolymer of maleic anhydride and sodium styrene sulfonate.

EXAMPLE III

The in vitro formation of hydroxyapatite (HAP) was measured titrimetrically using the pH - stat method described in Example I, above. The tests were conducted at pH of 7.20 at 25° C. and with calcium ion and phosphate ion concentration each at $3.85 \times 10^{-3}$M. Results of the experiments conducted in the presence of salivary enzyme i.e. pyrophosphatase, and anticalculus agents, are summarized in Table B below:

TABLE C

| Anticalculus Agent Composition | Mol. Wt. | Dosage (ppm) | Pyro phosphate | Pyrophos- phatase | Time of Crystal Growth Inhibition (min) |
|---|---|---|---|---|---|
| None | — | — | No | No | 12 |
| None | — | — | Yes | No | 30 |
| None | — | — | Yes | Yes | 11 |
| MEMA (50/50) | 70,000 | 35 | Yes | Yes | 12 |
| AA:MAA:t-BuAm (60:20:20) | 10,000 | 35 | Yes | Yes | >400 |

The results shown in Table C show that pyrophosphate significantly delays HAP forma;tion. The pyrophosphate was used at the level of 25 ppm. However, in the absence of an anticalculus agent polymer, the effectiveness of pyrophosphate is drastically reduced when incubated with enzyme, as evidenced by shorter delay time. This reduction is efficacy is due.to the enzymatic hydrolysis of P—O—P bonds. As demonstrated in the above table, the polymer composition of present invention is effective anticalculus agent espeacially in the presensce of both pyrophosphate and salivary enzymes. As demonstrated in Tables A and B, other copolymers will be effective as HAP crystal-growth inhibitors in the presence of salivary enzymes and pyrophosphates.

What is claimed is:

1. An oral composition comprising:
   (a) an effective amount of a fluoride source,
   (b) effective amount of a dental abrasive; and
   (c) 0.01 to 10% by weight of an anticalculus agent selected from homopolymers of monounsaturated monocarboxylic and dicarboxylic acids of 3 to 5 carbon atoms, salts and anhydrides thereof, and from copolymers containing at least 30% by weight of a carboxylic monomer selected from said acids, and mixtures of such anticalculus agents.

2. Composition of claim 1 wherein at least one comonomer of said copolymer is selected from acrylamides, alkyl acrylates, alkyl itaconates, vinyl sulfonic acid, hydroxyalkyl acrylates, alkoxyalkyl acrylates, lowe- ralkenyl carboxylates, styrene sulfonic acids, allyloxyhydroxyalkane sulfonic acids, acrylamidoalkane sulfonic acids, phosphonoalkane carboxylic acids, sulfoalkyl acrylates, salts and anhydrides thereof, and mixtures of such comonomers.

3. Composition of claim 2 wherein amount of said fluoride source is 0.005 to 3.0% by weight of said oral composition, wherein amount of said carboxylic monomer is 40 to 90% in said copolymers, and wherein molecular weight of said homopolymers and said copolymers is in the range of about 400 to 100,000.

4. Composition of claim 3 wherein said copolymer contains 60 to 10% of at least one of said comonomers, wherein amount of said fluoride source is 0.05 to 1%, and wherein amount of said anticalculus agent is 0.1 to 5%.

5. Composition of claim 5 wherein said carboxylic monomer is selected from acrylic acid, methacrylic acid, itaconic acid, maleic acid and its anhydride, citraconic acid, mesaconic acid, salts of such acids, and mixtures thereof; where acrylamides are defined as follows:

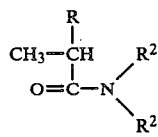

where R is selected from hydrogen and methyl groups; and $R^1$ and $R^2$ are individually selected from hydrogen and alkyl groups of 1 to 12 carbon atoms; where alkyl acrylates are defined as follows:

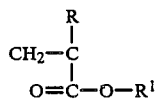

where R is selected from hydrogen and methyl groups and $R^1$ is selected from alkyl groups of 1 to 6 carbons and substituted alkyl groups where R' is defined as $R^2$ is an alkyl group of 1 to 6 carbons and Y is selected from $SO_3X$, —$COR^3$, and —$CO_2X$ where Y is selected from hydrogen, alkali metals alkaline earth metals, and ammonium groups and R3 is selected from alkyl groups of 1 to 3 carbons; where alkyl itaconates are defined as follows:

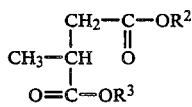

where $R^2$ and $R^3$ are individually selected from hydrogen and alkyl groups of 1 to 4 carbon atoms provided that both $R^2$ and $R^3$ are not hydrogens although either $R^2$ or $R^3$ can be hydrogen; where vinyl sulfonic acid and salts thereof are defined as follows:

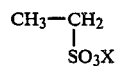

where X is selected from hydrogen, alkali metals, alkaline earth metals, and ammonium radicals; where hydroxyalkyl acrylates are defined as follows:

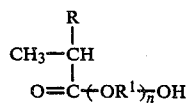

where R is selected from hydrogen and alkyl groups of 1 to 3 carbons, $R^1$ is selected from alkylene groups of 2 to 4 carbons, and n is from 1 to 5; where alkoxyalkyl acrylates are defined as follows:

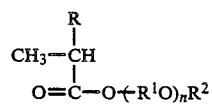

where R is selected from hydrogen and methyl groups, $R^1$ is selected from alkylene groups of 2 to 4 carbons, $R^2$ is selected from alkyl groups 1 to 10 carbons, and n is from 1 to 5; where lower alkenyl carboxylates are defined as follows:

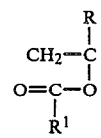

where R is hydrogen or a lower alkyl group of 1 to 6 carbon atoms, and $R^1$ is selected from alkyl groups of 1 to 12 carbon atoms; where vinyl alcohol is defined as follows:

where R is hydrogen or a lower alkyl group of 1 to 6 carbon atoms; where styrene sulfonic acids and salts thereof are defined as follows:

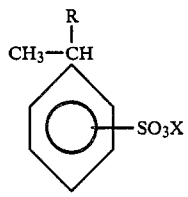

where R is selected from hydrogen and alkyl groups of 1 to 6 carbons, and X is selected from hydrogen, alkali metals, alkaline earth metals and ammonium radicals; where allyloxy hydroxyalkane sulfonic acids and salts thereof are defined as follows:

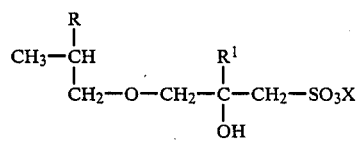

where R and $R^1$ are individually selected from hydrogen and methyl groups, and X is selected from hydrogen, alkali metals, alkaline earth metals, and ammonium radicals; where acrylamidoalkane sulfonic acids and salts thereof are defined as follows:

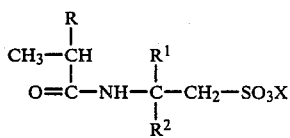

where R is selected from hydrogen and methyl groups, $R^1$ and $R^2$ are individually selected from hydrogen and alkyl groups of 1 to 4 carbons, X is selected from hydrogen, alkali metals, alkaline earth metals, and ammonium radicals; and where sulfoalkyl acrylates are defined as follows:

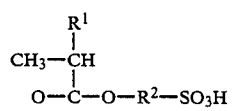

where $R^1$ is selected from hydrogen, methyl, and the group defined as

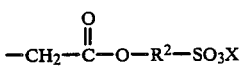

where $R^2$ is selected from alkylene groups of 1 to 12 carbon atoms and X is selected from hydrogen, alkali metals, alkaline earth metals, and ammonium radicals.

6. Composition of claim 5 wherein said acrylamides, both $R^1$ or $R^2$ are not hydrogens; where in said alkyl acrylates, $R^1$ is selected from unsubstituted alkyl groups of 1 to 4 carbons; where in said alkyl itaconates $R^2$ and $R^3$ are individually selected from unsubstituted alkyl groups of 1 to 4 carbons; wherein said sulfonic acid and salts thereof, X is selected from alkali metals and ammonium radicals; where in said hydroxyalkyl acrylates, R is selected from hydrogen and methyl groups and $R^1$ is selected from alkylene group of 2 to 3 carbons; wherein said alkoxyalkyl acrylates, $R^1$ is selected from alkylene groups of 2 to 3 carbons, $R^2$ is selected from alkyl groups of 1 to 4 carbons, and n is from 1 to 3; where in said styrene sulfonic acids and salts thereof, R is hydrogen, X is selected from hydrogen, ammonium and alkali metal radicals, and said $-SO_3X$ group is located at the 3 or 4 position on said phenyl ring; wherein said acrylamidoalkane sulfonic acid and salts thereof, R is hydrogen and $R^1$ and $R^2$ are individually selected from alkyl groups of 1 to 3 carbons; and where in said sulfoalkyl acrylates, $R^2$ is selected from alkylene groups of 2 to 4 carbons and X is selected from hydrogen, sodium, potassium, calcium, magnesium, and ammonium radicals.

7. Composition of claim 6 having pH of 6 to 10 which is effective in inhibiting formation of dental calculus wherein amount of said fluoride source is sufficient to supply from about 50 ppm to about 2,500 ppm of fluoride ions; wherein amount of said anticalculus agent is 1 to 1000 ppm; wherein amount of said dental abrasive is 10 to 70%; and wherein said composition also includes an oral vehicle.

8. Composition of claim 7 wherein amount of said abrasive is 0.1 to 7% by weight of a polyphosphate selected from alkali metal hexammetaphosophate, alkali metal tripolyphosphate, dialkali metal diacid, trialkali metal monoacid, alkali metal tripolyphosphate, tetraalkali metal pyrophosphate, hydroxyethylethane diphosphonic acid, and mixtures thereof.

9. Composition of claim 6 wherein amount of said calculus agent is 1 to 55, said copolymeric anticalculus agents have molecular weight of 2,000 to 20,000 and said monounsaturated carboxylic acid is selected from acrylic acid, methacrylic acid, maleic acid or its anhydride, itaconic acid, and mixtures thereof.

10. Composition of claim 9 wherein said anticalculus agent is selected from the following copolymers:
    (a) 60:20:20 copolymer of AA:MAA:t-BuAm
    (b) 63:37 copolymer of AA:HPA
    (c) 51:49 copolymer of AA:AMPS
    (d) 100 homopolymer of maleic acid
    (e) 100 homopolymer of acrylic acid
wherein the contractions used above are defined as follows:
    AA=acrylic acid
    MAA=methacrylic acid
    HPA=hydroxypropyl acrylate
    AMPS=2-acrylamido-2-methylpropane sulfonic acid.

11. Composition of claim 5 in toothpaste form wherein said fluoride source is selected from sodium fluoride, stannous fluoride, sodium monofluorophosphate, and mixtures thereof; amount of said dental abrasive is 10 to 75% and said dental abrasive is selected from silica, hydrated aluminum, insoluble metaphosphates, thermosetting polymerized resins, and mixtures thereof; and amount of said oral vehicle is 10 to 90% by weight.

12. Method of inhibiting dental calculus comprising applying to oral cavity composition as defined in claim 1.

13. Method of inhibiting dental calculus comprising applying to oral cavity composition as defined in claim 3.

14. Method of inhibiting dental calculus comprising applying to teeth composition as defined by claim 4.

15. Method comprising applying to teeth composition as defined by claim 5.

16. Method comprising applying to teeth composition as defined by claim 7.

17. Method comprising applying to teeth composition as defined by claim 11.

* * * * *